United States Patent [19]

Bianchin et al.

[11] Patent Number: 4,841,095
[45] Date of Patent: Jun. 20, 1989

[54] MODIFIED POLYISOCYANATES WITH BIURET STRUCTURE AND PROCESS FOR THEIR PREPARATION

[75] Inventors: Eugenio Bianchin, Treviso; Giovanni Longo, Spinea; Gian F. Lunardon, Paduva, all of Italy

[73] Assignee: Montedison S.p.A., Milan, Italy

[21] Appl. No.: 134,595

[22] Filed: Dec. 16, 1987

Related U.S. Application Data

[63] Continuation of Ser. No. 23,952, Mar. 11, 1987, abandoned, which is a continuation of Ser. No. 784,572, Oct. 4, 1985, abandoned.

[30] Foreign Application Priority Data

Oct. 5, 1984 [IT] Italy ................. 23003 A/84

[51] Int. Cl.$^4$ ........................... C07C 125/06
[52] U.S. Cl. .................... 560/115; 560/159
[58] Field of Search ............ 560/335, 115, 159

[56] References Cited

U.S. PATENT DOCUMENTS

| | | | |
|---|---|---|---|
| 4,028,392 | 6/1977 | Ogawa et al. | 260/453 AB |
| 4,386,032 | 5/1983 | Hughes et al. | 260/453 AB |
| 4,419,293 | 12/1983 | Hudson | 260/453 AB |

*Primary Examiner*—Alan Siegel
*Attorney, Agent, or Firm*—Stevens, Davis, Miller & Mosher

[57] ABSTRACT

Modified polyisocyanates with biuret structure containing terminal urethane groups and having general formula:

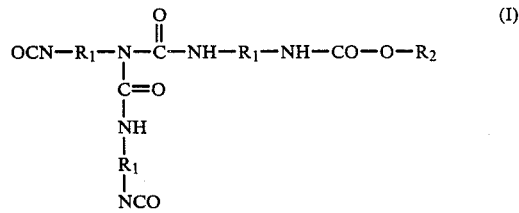

in which $R_1$ is an aliphatic, cycloaliphatic or aliphatic-cycloaliphatic radical, simple or substituted, and $R_2$ can have the same meanings as $R_1$ or can be the radical $R_3(OC_nH_{2n})_x-$.

Process for the preparation of modified polyisocyanates having biuret structure containing terminal urethane groups having general formula (I) consisting in reacting an organic diisocyanate with water or with a compound which splits off water, in the presence of a compatibilizing agent having a hydrogen atom reactive towards the isocyanate group, as it can be determined by Zerewitinoff's method.

15 Claims, No Drawings

MODIFIED POLYISOCYANATES WITH BIURET STRUCTURE AND PROCESS FOR THEIR PREPARATION

This application is a continuation of application Ser. No. 023,952, filed Mar. 11, 1987, now abandoned, which in turn is a continuation of application Ser. No. 784,572, filed Oct. 4, 1985, now abandoned.

BACKGROUND OF THE INVENTION

As is known, polyisocyanates having biuret structure are obtained by reacting three moles of an organic diisocyanate with one mole of an adduct-producing agent.

The term "organic diisocyanate", as used in the present specification and claims, is intended to mean the compounds having general formula:

$$OCN-R_1-NCO \qquad (II)$$

wherein $R_1$ is aliphatic, cycloaliphatic or aliphatic-cycloaliphatic radical which can or cannot be substituted with halogen, such as chlorine, $NO_2$, and alkyl radical, an alkoxy radical, non-reactive oxydryl groups, etc.

Examples of organic diisocyanates are: ethylidendiisocyanate, butylene diisocyanate, pentamethylene diisocyanate, hexamethylene diisocyanate, cyclopentylene-1,3-diisocyanate, cyclohexylene-1,4-diisocyanate, cyclohexylene-1,2-diisocyanate, hexahydroxy xylylenediisocyanate, dichloro-hexamethylenediisocyanate, dicyclo-hexyl-4,4'-diisocyanate, 1,2-di(isocyanatomethyl)cyclobutane, 1-methyl-2,4-diisocyanate-cyclohexane, 1-methyl-2,6-diisocyanate cyclohexane, etc.; aliphatic diisocyanates containing ethereal groups such as 1,3-bis-(γ-isocyanatopropoxy)-2,2-dimethyl-propane, etc.

Suitable adduct-producing agents are: water, water contained in compounds in the form of crystallization water or at the nascent state, formic acid, chlorohydrates, hydrate alcohols, monovalent tertiary alcohols, dicarboxylic acids which can be changed into their anhydrides such as oxalic acid, maleic acid, salicylic acid, etc., sulphide acid, primary and secondary amines, diamines, polyamines, etc.

Processes for the production of polyisocyanates having biuret structure using the above-mentioned adduct-producing compounds are described in U.S. Pat. Nos. 3,124,605, 3,350,438, 3,358,010, 3,392,183, 3,862,973, 3,896,154, 4,051,165, 4,147,714, 4,176,132, 4,218,390, 4,320,068, etc.

As is known, the reaction of an organic diisocyanate having formula (II) with an adduct-producing agent leads to the formation of an ureic bond ($R_1$—NH—CO—NH—$R_1$) which further reacts with isocyanic groups to form a tri-or poly-functional polyisocyanate.

The reaction can be schematized as follows when water is used as adduct-producing agent:

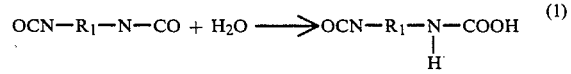  (1)

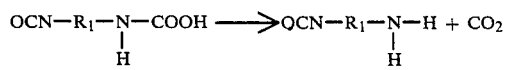  (2)

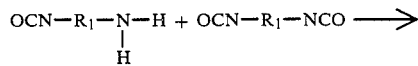  (3)

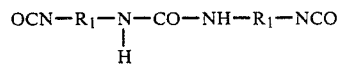

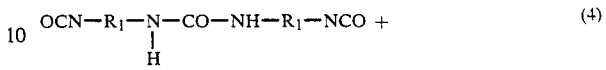

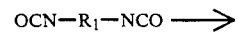

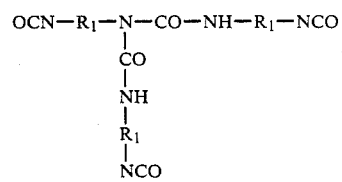

The thus formed polyisocyanate having biuret structure is soluble in common organic solvents such as toluene, xylene, acetic acid esters, etc.

The hereinabove reported reactions 1-4 are consecutive, but bifunctional urea or oligomers containing ureic bonds which form during the reactions can be solid or slightly soluble in the reaction medium and/or with the thus-formed polyisocyanate product. This makes the final product muddy and involves problems of deposit and clogging in the production plant.

However, while, on one hand, it is desirable that the ureic groups (NH—CO—) react with the isocyanic groups (OCN—), on the other hand, a polyisocyanate devoid of free ureic groups has high viscosity specially when its molecular weight is high.

A very viscous polymer is scarcely miscible in other resins or in solvents and, therefore, it is not suitable for being used, for example, in paint without negatively affecting the filmogenic and physical properties of the paint itself.

It has been proposed to use an excess of the organic diisocyanate in respect to the adduct-producing agent to produce polyisocyanates having biuret structure, devoid of free ureic groups and with low molecular weight.

Thus, U.S. Pat. No. 3,903,127 describes a process for the preparation of polyisocyanates with biuret structure wherein the molar ratio diisocyanate/adduct-producing agent is at least 11:1. This solution of the problem is not free of inconveniences due both to the stripping of the free diisocyanate and to the eventual thermal polymerization of the excess diisocyanate with formation of colored products such as uretidions, isocyanates, carbodiamidic bonds, etc.

Another inconvenience which arises during the preparation of polyisocyanates having biuret structure is that the adduct-producing agents are generally slightly soluble or completely insoluble in diisocyanate. Thus, for example, when water is used as adduct-producing agent, emulsions are obtained due to the low miscibility of water in organic diisocyanate. The reaction between water and the diisocyanate monomer dissolved in the aqueous phase leads to the formation of polyureas which precipitate as by-product. The precipitation of polyureas is not only economically disadvantageous, but it reduces the commerical value of the final polyisocyanate.

The amount of polyureas as by-product varies according to temperature, stirring speed, diisocyanate/water ratio, etc., but generally it always exceeds 0.5% by weight with respect to the final polyisocyanate. This amount of polyurea can be minimized by adding 40 moles or more of diisocyanate monomer per mole of water. A high excess of diisocyanate, however, does not completely eliminate the formation of polyureas and, in addition, it involves the problem of eliminating the large excess of non-reacted monomer.

In order to prevent the formation of polyureas as byproduct, it is proposed, in U.S. Pat. 4,028,392 to prepare a polyisocyonic prepolymer by reacting a diisocyanate with water in an organic hydrophilic solvent capable of dissolving both the water and the organic diiscyanate to form a homogeneous phase. The hydrophilic solvents proposed in said patent must not be reactive with the isocyanate group and are selected from the esters of carboxylic acids, esters-amides of phosphoric acid, ketones, nitrilies, ethers, etc., such as methyl-cellosolve acetate, cellosolve acetate, methyl-butyl-ketone, trimethylphosphate, di-methyl-formamide propionitrile, adiponitrile, etc.

However, this technique too is not free of drawbacks due to the removal of said solvents at the end of the reaction. In fact, incomplete removal of the solvent affects the physical properties of products such as varnishes or paints, obtained from polyisocyanates.

THE PRESENT INVENTION

An object of the present invention is to prepare a polyisocyanate having biuret structure which does not present the above mentioned inconveniences.

Another object of the present invention is to prepare a polyisocyanate having biuret structure which has low molecualr weight, reduced distribution of molecular weights and low viscosity so as to be miscible with other resins and solvents, and which is free of polyureas.

Still another object is to provide a process for the preparation of a polyisocyanate having biuret structure wherein precipitation of polyurea does not occur.

A further object is to provide a process for the preparation of a polyisocyanate having high quality biuret structure and essentially colorless.

According to the present invention, these and other objects are achieved, according to an embodiment, by way of a modified polyisocyanate having biuret structure containing terminal urethane groups and having general formula:

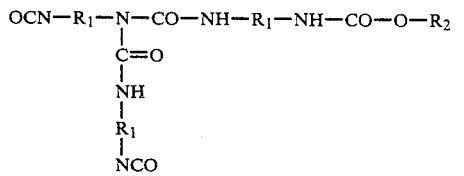

wherein $R_1$ is an aliphatic, cycloaliphatic or aliphatic-cycloaliphatic non-substituted radical or where one or more hydrogen atoms can be substituted by a halogen, such as chlorine, $NO_2$, a non-reactive oxydryl, an alkyl radical or an alkoxy radical; $R_2$ can have the same meanings as $R_1$ or can be the radical:

$$R_3(OC_nH_{2n})_x-\qquad\qquad (IV)$$

wherein $R_3$ is an alkyl or acetyl radical having up to 18 carbon atoms, n is a whole number ranging between 2 and 4 and x is a whole number ranging between 1 and 50.

According to another embodiment of the present invention, the foregoing objects are achieved by means of a process for the preparation of modified polyisocyanates with biuret structure having formula (I), which consists in reacting water or a compound which splits off water with an organic diisocyanate, in a molar ratio diisocyanate/water lower than 10:1, in the presence of a compatibilizing agent having a hydrogen atom reactive towards the isocyanate group, as determined by Zerewitinoff's method.

The process according to the present invention does not only prevent the formation of polyureas as by-product, but it also allows to obtain modified polysocyanates with biuret structure having a reduced distribution of molecular weights, viscosity less than 10,000 mPa.s. at 25° C. and low molecular weight, particularly suitable for being used in the paint industry.

The compatibilizing agents which can be used in the practice of the present invention are those capable of forming a homogeneous phase with water and diisocyanate under the reaction conditions and for the whole reaction period.

The compatibilizing agents having boiling point exceeding 80° C. are preferred, so that, under the reaction conditions, they do not evaporate before interacting with the isocyanic groups.

Compatibilizing agents having boiling points ranging between 80° C. and 200° C. are preferred.

The quantity of said compatibilizing agents is not critical and can very according to the type of diisocyanate, to the solvents used and to the reaction conditions. In general, very small amounts, generally less than 10 parts by weight of compatibilizing agent per one part by weight of water, are sufficient to obtain excellent results.

Water/compatibilizing agent ratios by weight ranging between 9:1 and 1:9 and preferably between 2:1 and 1:2 can be used. In practice, a water/compatibilizing agent ratio by weight of 1:1 is preferably used.

The use of said compatibilizing agents having a hydrogen atom reactive with the isocyanate group makes it possible to obtain polyisocyanates having the required properties, by using molar ratios of diisocyanate and water lower than those known in the art; as a consequence, the quantity of residual diisocyanate to be evaporated at the end of the reaction is far smaller. Futhermore, because the compatibilizing agents are reactive with isocyanic groups, they are fixed with formation of urethane bonds and therefore their removal at the end of the reaction is not necessary.

Suitable compatibilizing agents having a hydrogen atom reactive with isocyanate group which can be used in the process according to the present invention are monooxydryl compounds $R_2$—OH (III) wherein OH is a primary oxydryl with high polarity and $R_2$ has the same meaning as $R_1$ or can be the radical:

$$R_3(OC_nH_{2n})_x-\qquad\qquad (IV)$$

wherein $R_3$ is an alkyl or acetyl radical having up to 18 carbon atoms, n is a whole number ranging between 2 and 4 and x is a whole number ranging between 1 and 50.

Examples of compatibilizing agents which can be used advantageously in the process of this invention are: polyoxythylene monoethylether, polyoxyethylene monobutylether, polyoxybutylene monoethylether, polyoxybutylene monobutylether, polyoxyethylene monoacetate, polyoxybutylene omonacetate, cellosolve, butyl-cellosolve and higher homologues, ethylene glycol acetate, butylene glycol acetate, ethyl monoester of glycolic acid, butyl monoester of glycolic acid, etc.

The water used as adduct-producing agent, according to the present invention, can be either as such or in the form of compounds which split off water, such as: compounds containing crystallization water, such as for instance; sodium sulphate, oxalic acid, hydrate formaldehyde, bicarboxylic acids which easily change into anhydrides, such as, for example, maleic acid and salicylic acid, etc.

Organic diisocyanates which can be used in the process according to the present invention are those having general formula (II) as reported hereinabove. Hexamethylene diisocyanate is particularly preferred.

The reaction for the formation of biuret can be carried out both in the presence and in the absence of catalysts. In the latter case, the catalysts generally used in the reaction betwen water and diisocyanate can be used.

Examples of said catalysts are: tertiary amines, such as triethylene diamine, N-ethyl-ethyleneimine, tetramethylguanidine, dimethylcyclohexylamine, dimethylethanolamine, etc., and organometallic activators such as dibutyltindilaurate, tin octoate, cobalt naphthenate, vanadium acetylacetonate, dimethyl-tindiethylhexaneate and their mixtures.

The preferred catalysts are the organometallic ones, which proved to be much more active in the present process. They, however, must be used in very low concentrations, generally less than 0.5% by weight with respect to diisocyanate, in order to avoid that the product passes from low and applicatively acceptable viscosity, obtained at the end of the reaction, to viscosities increasing in time, specially if the product is stored at a temperature exceeding ambient temperature or under continuous stirring. For this reason, it is generally preferable not to use a catalyst during the stage of biuret preparation. Catalysts of high activity preferred for use in the process according to the present invention are: tinoctoate and dibutyltindilaurate.

During the reaction, it is preferred to maintain the reaction medium under vigorous stirring to facilitate good dispersion of the adduct-producing agent into the diisocyanate and to make the separation of ureas and polyureas more difficult.

The reaction temperature ranges from 80° C. to 200° C. and preferably from 130° to 190° C., in order to obtain a high reaction rate even in the absence of catalysts and, at the same time, to avoid phenomena of yellowing of the product.

It is preferred to first carry out the mixture of water and compatibilizing agent and then add the mixture thus obtained to diisocyanate, deaerated and preheated at the above-reported reaction temperature, under continuous stirring. The water-compatibilizing agent mixture is added in a way that the molar ratio diisocyanate/water in total ranges between 5:1 and 10:1, preferably around 7:1. Furthermore, the feeding rate is adjusted so as to keep the reaction temperature as constant as possible.

When the addition of the water-compatibilizing agent mixture is over, the reaction medium is kept under stirring at constant temperature for the minimum time necessary for completion of the reaction, which can be determined, for example, by testing viscosity.

At the end of the reaction, the excess of diisocyanate is recovered from the reaction mixture at the lowest possible temperature in order to avoid formation of oligomers and/or colored products. A thin layer evaporator or a molecular distillator can, for example, be used. A modified polyisocyanate with biuret structure is obtained containing terminal urethane groups, having a free diisocyanate content lower than 0.5% by weight.

As mentioned above, the process according to the present invention is carried out in homogeneous phase in the presence of a compatibilizing agent between diisocyanate and the adduct-producing agent and which is reactive towards diisocyanate. The final product mainly consists of diisocyanate biuret and possibly its higher homologues, modified by the presence of terminal urethane groups deriving from the compatibilizing agent used.

The product obtained has viscosity lower than 10,000 mPa.s. at 25° C., preferably lower than 5,000 mPa.s., a restricted distribution of molecular weights, a titer ranging between 21 and 23% of free NCO and a complete solubility in toluene at 10% by weight for at least 4 hours.

The reaction system can be additioned with coloration inhibitors, UV stabilizers, catalysts and other additives which are well known to those skilled in the art for the production of polyisocyanates.

The following examples are given only to illustrate the invention in more detail and are not intended to be limiting.

Unless otherwise indicated, all the parts, percentages and ratios referred to in the examples are by weight.

EXAMPLE 1

0.17 parts of catalyst dibutyltindilaurate are added to 350 parts of hexamethylene diisocyanate contained in a flask provided with stirrer, reflux condenser, thermometer and feeding inlets and the mixture is heated under a light flow of dry $N_2$ up to 140° C. 10.7 parts of a previously prepared 1:1 mixture of water/butylcellosolve are then added dropwise and under vigorous stirring.

The speed at which the mixture is fed is such as to maintain the temperature within ±3° C.

Precipitates or cloudiness are not observed during the reaction, which is shown by continuous regular emission of $CO_2$ gas. When feeding is over, the reaction mass is kept at the indicated temperature and under stirring for 15 minutes more. The excess monomer is then recovered by distillation at 140° C. and 0.5–1 residual mmHg.

The final product is a liquid, of coloration lower than 1 gardner, having 22.8% titer free NCO, viscosity at 25° C. of 1830 mPa.s and a residual hexamethylene diisocyanate content lower than 0.5% by weight, determined by chromatographic analysis.

A 10% solution of the resulting product in toluene does not show turbidity after 4 hours.

EXAMPLE 2

Using the same procedure and quantities as in Example 1 except for the absence of a catalyst and heating the reaction mass up to 180° C., a clear liquid final product is obtained of color less than 1 gardner, having 22.6% titer free NCO, viscosity at 25 C. of 1580 mPa.sec. and residual hexamethylene diisocyanate content lower than 0.5%, determined by means of chromatographic analysis.

The product dissolved in 10% toluene does not present any turbidity after 4 hours.

EXAMPLE 3

Using the same procedure and quantities as in Example 1, except for the use of 12.5 parts of a 1:1 mixture of water/butylcellosolve, a clear liquid final product is obtained of color less than 1 gardner, having 21.6% titer of free NCO, viscosity at 25° C. of 4,400 mPa.secl and residual hexamethylene diisocyanate content lower than 0.5%, determined by chromatographic analysis.

A 10% solution of the product in toluene shows no turbidity after 4 hours.

EXAMPLE 4

Example 3 is repeated but using a water/ethyleneglycol acetate mixture in 1:1 ratio, a clear liquid final product is obtained of color less than 1 gardner, having 21.9% titer of free NCO, viscosity at 25° C. of 3,800 mPa.s. and residual hexamethylene diisocyanate content lower than 0.5% determined by chromatographic analysis.

A 10% solution of the product in toluene shows no turbidity after 4 hours.

EXAMPLE 5

Example 4 is repeated but using a water/butylester of glycolic acid mixture. A clear final product is obtained of color less than 1 gardner, having 22.5 titer of free NCO, viscosity at 25° C. of 4,500 mPa.s and residual hexamethylene diisocyanate content lower than 0.5% and determined by chromatographic analysis.

A solution of the product in 10% toluene does not present any turbidity after 4 hours.

What we claim is:

1. A process for the preparation of modified polyisocyanates having a biuret structure as set forth below:

$$OCN-R_1-HN-\overset{\overset{O}{\|}}{C}-\underset{\underset{NCO}{\overset{|}{R_1}}}{N}-\overset{\overset{O}{\|}}{C}-NH-R_1-NH-COOR_2$$

wherein $R_1$ is radical selected from the group consisting of unsubstituted aliphatic, cycloaliphatic and aliphatic-cycloaliphatic radicals, said radicals having one or more hydrogen atoms substituted by halogen, $NO_2$, a non reactive hydroxy, an alkyl radical or an alkoxy radical; and $R_2$ is the radical $R_3(OC_nH_{2n})_x-$ wherein $R_3$ is an alkyl or acetyl radical having a maximum of 18 carbon atoms, n is a whole number selected from 2, 3 and 4 and X is a whole number selected from 1 to 50, the process consisting of reacting water or a compound containing water of crystallization which splits off water, with an organic diisocyanate, in a diisocyanate/water molar ratio lower than 10:1, in the presence of an agent which forms a homogeneous phase with water and the diisocyanate under the reaction conditions and throughout the reaction period, and which has a hydrogen atom which reacts with the isocyanate group as determined by the Zerewitinoff method.

2. Thd process of claim 1, wherein the agent which forms a homogeneous phase with water and the diisocyanate under reaction conditions has a boiling point exceeding 80° C.

3. The process of claim 2, wherein the agent which forms a homogeneous phase with water and the diisocyanate under reaction conditions has a boiling point of 80° C. to 200° C.

4. The process of claim 1, in which the amount of the agent which forms a homogeneous phase with water and the diiscoyanate under reaction conditions is less than 10 parts by weight for one part by weight of water.

5. The process of claim 4, in which the ratio by weight of water/agent which forms a homogeneous phase with water and the diisocyanate under reaction conditions is from 9:1 to 1:9.

6. The process of claim 4, in which the ratio by weight of water/agent which forms a homogeneous phase with water and the diisocyanate under reaction conditions, is from 2:1 to 1:2.

7. The process according to claim 4, wherein the ratio by weight of water/agent which forms a homogeneous phase with water and the diisocyanate under reaction conditions is 1:1.

8. The process according to claim 1, wherein the diisocyanate/water molar ratio is from 5:1 to 10:1.

9. The process of claim 8, in which the diisocyanate/water molar ratio is about 7:1.

10. The process of claim 1, in which the agent which forms a homogeneous phase with water and the diisocyanate under reaction conditions having a hydrogen atom which reacts with isocyanate group is a hydroxy $R_2$—OH compound wherein —OH is a primary hydroxy of high polarity and $R_2$ is a radical:

$$R_3(OC_nH_{2n})_x— \qquad [IV]$$

wherein $R_3$ is an alkyl or acetyl radical having a maximum of 18 carbon atoms, n is a whole number from 2 to 4 and x is a whole number from 1 to 50.

11. The process of claim 10, in which the agent which forms a homogeneous phase with water and the diisocyanate under reaction conditions is butylcellosolve.

12. The process of claim 1, in which the reaction is carried out at a temperature from 80° to 200° C.

13. The process of claim 12, in which the reaction is carried out in the presence of an organometallic catalyst.

14. The process of claim 13, in which a catalyst is used and is tin-octooate.

15. The process of claim 13, in which a catalyst is used and is dibutyl-tindilaurate.

* * * * *